United States Patent [19]

Desideri et al.

[11] Patent Number: 4,758,567
[45] Date of Patent: Jul. 19, 1988

[54] 7-(4-AMINO-PIPERAZINYL)- OR 7-(4-CHLORO-PIPERAZINYL)QUINOLINONE AND AZAQUINOLINONE DERIVATIVES AND PHARMACEUTICAL COMPOSITIONS CONTAINING THEM

[75] Inventors: Desiderio Desideri; Riccardo Stradi; Alberto Milanese, all of Monza, Italy

[73] Assignee: Rottapharm S.p.A., Milan, Italy

[21] Appl. No.: 931,411

[22] Filed: Nov. 14, 1986

[30] Foreign Application Priority Data

Nov. 19, 1985 [IT] Italy ................. 22887 A/85
Nov. 19, 1985 [IT] Italy ................. 22888 A/85

[51] Int. Cl.⁴ .................. A61K 33/495; C07D 401/04
[52] U.S. Cl. .................. 514/254; 544/279; 544/362; 544/363
[58] Field of Search .......... 544/363; 514/254

[56] References Cited

U.S. PATENT DOCUMENTS 4,146,719  3/1979  Irikura .................. 544/363
4,670,444  6/1987  Grohe et al. .......... 544/363

FOREIGN PATENT DOCUMENTS 870917  2/1979  Belgium .
49355   4/1982  European Pat. Off. .
78362   5/1983  European Pat. Off. .
117473  9/1984  European Pat. Off. .
117474  9/1984  European Pat. Off. .
131839  1/1985  European Pat. Off. .
2341146 2/1974  Fed. Rep. of Germany .
2840910 4/1979  Fed. Rep. of Germany .

Primary Examiner—Glennon H. Hollrah
Assistant Examiner—James H. Turnipseed
Attorney, Agent, or Firm—Walter H. Schneider

[57] ABSTRACT

Compounds of formula I

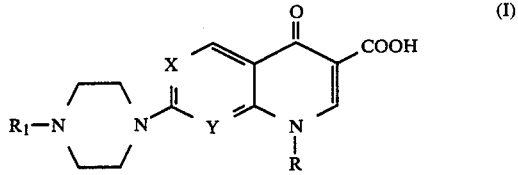

wherein:
X is N or $>$C—F;
Y is N, $>$C—F or $>$CH;
R is a $C_1$–$C_5$ alkyl or $C_3$–$C_6$ cycloalkyl group;
$R_1$ is selected from the group consisting of a chlorine atom, an amino group or a group of formula:

$$R^2-CH=N-$$

wherein $R_2$ is a $C_1$–$C_5$, straight or branched aliphatic residue or an optionally substituted aromatic or heteroaromatic residue, and addition salts thereof with pharmaceutically acceptable bases or acids, prepared starting from the corresponding compounds wherein $R_1$ is hydrogen, by reaction with organic hypochlorites or nitrous acid, are endowed with favorable therapeutic properties.

4 Claims, No Drawings

7-(4-AMINO-PIPERAZINYL)- OR 7-(4-CHLORO-PIPERAZINYL)QUINOLINONE AND AZAQUINOLINONE DERIVATIVES AND PHARMACEUTICAL COMPOSITIONS CONTAINING THEM

The present invention concerns compounds having antibacterial activity, a process for the preparation thereof and pharmaceutical compositions containing them. More particularly, the invention concerns compounds having the following general formula (I):

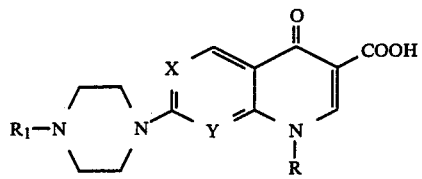

wherein:
X is N or $>C-F$;
Y is N, $>C-F$ or $>CH$;
R is a $C_1-C_5$ alkyl or $C_3-C_6$ cycloalkyl group;
$R_1$ is selected from the group consisting of a chlorine atom, an amino group or a group of formula:

$R^2-CH=N-$ wherein $R_2$ is a $C_1-C_5$, straight or branched aliphatic residue or an optionally substituted aromatic or heteroaromatic residue,
and addition salts thereof with pharmaceutically acceptable bases or acids.

Particularly preferred compounds according to the invention are those wherein both X and Y are nitrogen atoms or Y is a CH group whereas X is a $>C-F$ group.

Preferred meanings for R are methyl, ethyl or cyclopropyl groups.

Pharmaceutically acceptable acids include inorganic acids such as hydrochloric, hydrobromic, sulfuric and phosphoric acid; and organic acids such as toluenesulfonic, methanesulfonic, tartaric, citric, fumaric acids, etc.

Pharmaceutically acceptable bases include inorganic bases, such as alkali or alkali-earth metal cations; or organic bases, such as aliphatic amines, aminoacids, quaternary ammonium groups etc.

Some of the salts according to the invention often have special advantages due to an increased stability, ease of crystallization, lack of objectionable taste, etc., but these are all subsidiary to the main physiological action of the free base or acid.

Several compounds having quinoline-, naphthyridine-, pyrido-pyrimidine- or pyrimido-pyridine-like structures, having an unsubstituted or para-substituted piperazine residue are already known.

Said compounds are disclosed, for instance, in the following patents: BE No. 870,917, DE Nos. 2,341,146 and 2,840,910, EP No. 49355 and in the following european patent applications Nos. 78362, 117,473, 117,474 and 131,839.

Nevertheless, compounds having, as substituent on the nitrogen atom in position 4 of the piperazine ring, a chlorine atom or an amino group, optionally in form of hydrazones thereof, are unknown. Although the above cited patents or applications disclose compounds having a satisfactory antibacterial activity, some of them being already used in human therapy, there is however a constant need for new drugs which are endowed either with a wider antibacterial spectrum and/or with a lower rate of side-effects which are typical of the drugs up to now used, or also with better pharmacokinetics characteristics.

In particular, compounds of formula I, with respect to the known compounds, exhibit an higher urinary excretion which, in addition to a remarkable antibacterial activity, makes them even more effective in the treatment of the urinary tract infection sustained by Gram positive and Gram negative bacteria.

In this respect, the compounds of the invention may be administered by the oral or parenteral route, in form of appropriate pharmaceutical compositions providing a further object of the invention.

The formulation of suitable pharmaceutical compositions may be carried out according to techniques well-known in the art, such as the ones described in "Remington's Pharmaceutical Sciences Handbook", Hack Publishing Co., U.S.A.

For the oral administration, the compounds may be formulated in solid or liquid preparations, such as capsules, pills, tablets, powders, solutions, suspensions or emulsions. The unitary solid dose may be a gelatine capsule, both soft and hard, containing lubricants such as lactose, saccharose, starch or a tablet comprising conventional excipients, such as lactose, saccharose, starch, gelatine, alginic acid, stearic acid, magnesium stearate etc.

By parenteral administration the compounds I or salts thereof may be administered in injectable formulations, dissolved or suspended in physiologically acceptable diluents, with a vehicle that may be a sterile liquid such as water or an oil, with or without the addition of other excipients. Generally, as a vehicle for the injectable solution, water, aqueous solutions of mineral salts, aqueous solutions of dextrose or other sugars, ethanol, glycols may be used.

Several other substances may be used in addition of or in place of the above listed ones, as it is well known by any skilled in the art. It is understood that, even though they are not specifically herein described, all these formulations fall within the scope of the present invention.

The daily dosage will obviously depend on several factors such as, for instance, the sensitivity of the infecting bacterial strain, the age, body weight and conditions of the patient. Generally, 500 to 2000 mg/die of active principle, divided in 2-4 administrations, will be sufficient.

The compounds I wherein $R_1$ is a chlorine atom are prepared, according to the present invention, by reacting compounds of formula II

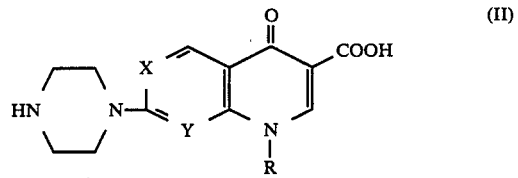

wherein R, X and Y have the above meanings with reagents able to supply $Cl^+$ ions such as N-chloro-succinimide, organic or inorganic hypochlorites, preferably t-butylhypochlorite, or with other equivalent chlorinating reagents, in inert solvents such as halogenated hydrocarbons and at temperatures ranging from 0° to 25° C., preferably from 5° to 10° C.

The compounds I wherein $R_1$ is an amino or an hydrazone group, are prepared according to the invention by reacting compounds II with nitrous acid: the obtained N-nitroso derivatives are then directly reduced to the compounds I by means of conventional reducing agents, for instance by means of Zn in acids. The so obtained compounds I may be then reacted with aldehydes of formula $R_2$—CHO, wherein $R_2$ has the above defined meanings.

The following examples further illustrate the invention without limiting the scope thereof.

EXAMPLE 1

3 G ($9.39 \times 10^{-3}$ moles) of norfloxacine (formula II, X=CF, Y=CH) were dissolved in 30 ml of dichloromethane. A solution of 1.02 g of ter-butyl hypochlorite ($9.39$ g$\times 10^{-3}$ moles) in 10 ml of dichloromethane, is added dropwise to the obtained solution, under stirring and keeping the temperature from 5° to 10° C.

The obtained suspension was left under stirring for 15 hours, then filtered and the residue was washed with cold ethyl acetate.

3 G (90% yield) of N-chloro-norfloxacine (formula I, X=CF, Y=CH), melting at 255° (dec.) were obtained.

IR spectrum: in agreement

Mass spectrum: $M^+=353$ m/e $^1$N-NMR (DMSO): δ(TMS):

1.45 (3H, triplet, $CH_2\underline{CH_3}$);
2.90–4.10 (8H, multiplet, piperazine);
4.65 (2H, quartet, $\underline{CH_2}CH_3$);
7.25 (1H, doublet, aromatic);
7.80 (1H, doublet, aromatic);
8.96 (1H, singlet, =CH);
9.90 (1H, singlet, COOH).

EXAMPLE 2

Following the same procedure of the Example 1, starting from pipemidic acid, the compound of formula I wherein X=Y=N and $R_1$ is chlorine, was obtained, m.p. 210° C. (dec.), IR: in agreement. Mass spectrum: 337 m/e.

$^1$H-NMR (DMSO): δ(TMS):

1.50 (3H, triplet, $CH_2\underline{CH_3}$);
2.90–4.00 (8H, multiplet, piperazine);
4.45 (2H, quartet, $\underline{CH_2}CH_3$);
8.90 (1H, singlet, aromatic);
9.20 (1H, singlet, =C—H);
11.0 (1H, singlet, COOH).

EXAMPLE 3

(a) 5 G ($1.56 \times 10^{-2}$ moles) of Norfloxacine were dissolved in 10 ml of water and 50 ml of acetic acid, under stirring. The obtained solution was cooled to 5° C. and 1.15 g of sodium nitrite ($1.67 \times 10^{-2}$ moles) dissolved in 10 ml of water, were added dropwise thereto, under stirring.

The reaction mixture was kept under stirring for 30 minutes, the formed precipitate was filtered, washed with water and dried in the air. 4.7 G of N-nitroso derivative, which was directly used in the subsequent step, were obtained.

M.p.>240° C.

(b) 4.6 G of N-nitroso-norfloxacine ($1.32 \times 10^{-2}$ moles), obtained in the step (a), dissolved in 40 ml of acetic acid, were added dropwise, under stirring, to a suspension of 3.45 g of zinc powder ($5.28 \times 10^{-2}$ moles) in 15 ml of water.

The mixture was allowed to react at room temperature for 4 hours, then warmed to 80° C., filtered and evaporated. The residue was washed with cold ethyl acetate, then dissolved in warm water and few isopropanol (5–10%). The solution was allowed to stand overnight and then filtered.

M.p. 252° (dec.).

IR (Nujol): in agreement.

Mass spectrum: in agreement.

Elementary analysis: in agreement.

$^1$H-NMR (TFA): δ(TMS):

1.80 (3H, triplet, $CH_2$—$\underline{CH_3}$);
3.75–4.30 (8H, multiplet, $CH_2$ piperazine);
4.95 (2H, quartet, $\underline{CH_2}$—$CH_3$);
7.60 (1H, doublet, aromatic);
8.35 (1H, doublet, aromatic);
9.35 (1H, singlet, =CH).

EXAMPLE 4

Following the procedure described in the Example 3, but starting from pipemidic acid, the compound I wherein $R_1$ is $NH_2$ and X and Y are nitrogen atoms, was prepared.

M.p.: 260° (dec.).

Mass spectrum: $M^+=318$ m/e.

Elementary analysis: in agreement.

IR (Nujol): in agreement.

$^1$H-NMR (TFA): δ(TMS):

1.78 (3H, triplet, $CH_2$—$\underline{CH_3}$);
3.70–4.60 (8H, multiplet, $CH_2$ piperazine);
4.90 (2H, quartet, $\underline{CH_2}$—$CH_3$);
8.95 (1H, singlet, aromatic);
9.25 (1H, singlet, =CH).

EXAMPLE 5

2 G of N-amino-norfloxacine (prepared according to the Example 3), were refluxed in methanol with 1.02 g ($6.17 \times 10^{-2}$ moles) of veratric aldehyde, for 24 hours. The reaction mixture was evaporated, the obtained residue was crystallized from ethanol, and crystallized again from methanol saturated with HCl. 2.40 G of the desired compound (yield: 80% with reference to the N-nitroso derivative).

M.p. (dec.): higher than 200° C.

Mass spectrum: $M^+$ 482 m/e.

IR: in agreement.

Elementary analysis: in agreement.

$^1$H-NMR (TFA): δ(TMS):

1.80 (3H, triplet, $CH_2$—$\underline{CH_3}$);
3.75–4.45 (14H, multiplet, $CH_2$ piperazine);
4.95 (2H, quartet, $\underline{CH_2}$—$CH_3$);
7.15 (1H, doublet, aromatic);
7.45–7.85 (9H, multiplet, aromatic);
8.35 (1H, doublet, aromatic);
9.00 (1H, singlet, =CH hydrazone);
9.45 (1H, singlet, =CH).

We claim:

1. A compound of formula I

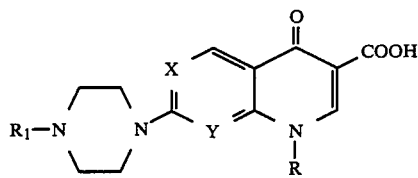

wherein:
X is >C—F;
Y is >C—F or >CH;
R is a $C_1$-$C_5$ alkyl or $C_3$-$C_6$ cycloalkyl group;
$R_1$ is selected from the group consisting of a chlorine atom, amino or a group of formula:

$$R_2-CH=N-$$

wherein $R_2$ is a $C_1$-$C_5$, straight or branched aliphatic residue,
and addition salts thereof with pharmaceutically acceptable bases or acids.

2. Compounds according to claim 1, wherein X is a CF group and Y is a CH group.

3. Compounds according to claim 1, wherein $R_2$ is a 3,4-dimethoxy-phenyl group.

4. A pharmaceutical composition having antibacterial activity containing as the principal active ingredient an effective amount of a compound according to claim 1 in admixture with a pharmaceutically acceptable carrier.

* * * * *